(12) United States Patent
Kuhn et al.

(10) Patent No.: US 6,443,731 B2
(45) Date of Patent: Sep. 3, 2002

(54) MEDICAL AND DENTAL HANDPIECE (75) Inventors: Bernhard Kuhn, Schemmerhofen; Bernd Gugel, Ulm-Einsingen, both of (DE)

(73) Assignee: Kaltenbach & Voigt GmbH & Co., Biberach/Riss ( * ) Notice: Subject to any disclaimer, the term of this patent is extended or adjusted under 35 U.S.C. 154(b) by 0 days.

(21) Appl. No.: 09/874,796

(22) Filed: Jun. 5, 2001

(30) Foreign Application Priority Data

Jun. 19, 2000 (DE) .......................................... 100 30 114

(51) Int. Cl.$^7$ ................................................. A61C 1/07
(52) U.S. Cl. ....................................... 433/118; 433/123
(58) Field of Search ................................. 433/105, 106, 433/114, 118, 123

(56) References Cited

U.S. PATENT DOCUMENTS 4,617,837 A 10/1986 Kataoka et al. ................ 74/785
5,454,718 A 10/1995 Strohmaier .................. 433/122
5,529,495 A * 6/1996 Edwards ...................... 433/112
5,924,864 A 7/1999 Logé ........................... 433/118
6,176,703 B1 1/2001 Gugel et al. ................. 433/120

FOREIGN PATENT DOCUMENTS

DE      197 45 245 A1    10/1998
WO      WO 99/58076      11/1999

* cited by examiner

Primary Examiner—Cary O'Connor
(74) Attorney, Agent, or Firm—Marshall, Gerstein & Borun (57) ABSTRACT The invention relates to a handpiece (3) for medical purposes, having a tool holder (5) arranged in the forward end region of the handpiece (3), a retaining coupling (16) for releasably fixing a tool (6) in the tool holder (5), and a drive connection (8), for a rotary and/or stroke drive of the tool holder (5), extending longitudinally through the handpiece (3), there being provided an arrangement for limiting the maximum torque value which can be transmitted to the tool holder (5) to a lesser torque value. For the purpose of broadening the range of application of the handpiece (3), the arrangement can be selectively deactivated and again activated, by means of a setting device (14).

25 Claims, 3 Drawing Sheets

MEDICAL AND DENTAL HANDPIECE

TECHNICAL FIELD

The invention relates to a handpiece as part of a treatment or working instrument or to a treatment or working device for medical purposes.

Such a handpiece may be, inter alia, a medical or dental treatment instrument or a working instrument for a medical or dental laboratory.

BACKGROUND OF THE RELATED ART

Medical or dental handpieces or treatment instruments differ, inter alia, in the functioning of the tool which they in each case carry and in the functioning of the drive. A tool may be driven by means of rotation, such as is for example the case with a drill, or by means of an axial stroke movement, such as is the case with a file, or also in a combination of these movements. A handpiece having a rotary driven tool can, with appropriate configuration of the tool, also be used for the purpose of transmitting a rotational drive force to rotary parts, for example to tighten or loosen screws present at the treatment site, such as is the case for example with screws of dental prostheses or other body parts.

In DE 197 45 245 A1 there is described a handpiece in combination with a tool for the preparation of a tooth root canal, wit h which the maximum torque which can be transmitted to the tool is limit ed to a particular lesser value. By these means, the tool is protected from overloading resulting from the drive, and damage to the tool or breakage of the tool are avoided. This known handpiece is thus restricted in its range of function or application.

SUMMARY OF THE DISCLOSURE

With the handpiece in accordance with the invention the arrangement reducing the torque can be selectively deactivated and activated again by means of a setting device. By these means it is possible to employ the handpiece both for those applications in which the maximum torque value should be reduced and also to employ it for those applications in which the maximum torque value made available by the drive present should be fully exploited. The handpiece in accordance with the invention is thus suitable not only for root canal preparation work but also for normal working and drive operations, such as for example material removing working, or turning and screw working on the human or animal body. It can thus be employed at a medical and/or dental treatment station and also at a technical workstation. The handpiece in accordance with the invention can thus be more effectively put to use not only with regard to its expanded range of application but also in the individual situation, for example when the maximum drive force of the drive present should temporarily be employed. This can for example be the case when, for the purpose of carrying out specific types of work, the danger of damage or breakage of the tool is not present or, for particular reasons, is to be accepted as a risk.

The arrangement for reducing or limiting to a particular torque value can be formed by means of an overload coupling which is preferably arranged in the handpiece, or by means of an electrical control device for controlling the electrical drive current for an associated electric motor.

For a handpiece of the kind under consideration there are two significant required features. On the one hand it should be readily operable, so that the operating person can pay more attention to the work to be carried out with the handpiece. On the other hand, the size of a handpiece is subject to restriction, because in the working of the human or animal body it must be put to use in many cases in body cavities, such as is for example the case with the mouth in a dental application. There thus exists the requirement on the one hand to manufacture the handpiece with dimensions as small as possible and on the other hand to ensure a simple and ready operation of the treatment instrument. A particularly advantageous configuration distinguishes itself in that a common setting member is provided both for the overload coupling and also for the direct coupling. By these means there is achieved not only a lesser number of components and thus also a lesser size, but also a simple and ready operation is possible because the operating person must actuate only one setting member. Thereby it is advantageous to so divide the range of movement of the setting member that in one range of movement the maximum transmissible torque can be set and in a second range of movement, joining on the first range of movement, the direct coupling can be engaged and disengaged. An advantageous place for the setting member is located on the outer surface of the treatment instrument, whereby a direction of movement for the setting member directed in the circumferential direction is excellently suited.

In order to avoid an unintended displacement of the setting member, it is advantageous to releasably position the setting member in each setting disposition, by means of a positioning device. For this purpose there is suited a preferably elastically yielding and thus manually overcomable positioning device, which makes it possible in a ready manner to overcome the positioning device concerned with a certain exercise of force. By these means special manual manipulations for releasing the positioning device are avoided.

If, with a treatment instrument of the kind under consideration, the overload coupling comes into function at an increased working resistance and the maximum transmittable torque is thereby restricted in that the mechanical overload coupling races or slips, there is a danger of a non-uniform transmittal of torque during the slippage, which arises in that the rotational engagement between the two coupling parts occurs erratically. This leads, despite to the slippage of the overload coupling, to sudden and repeated torque loading peaks. By these means there arises not only the danger that the tool will be overloaded due to the short term loading peaks, as a form of stick-slip effect, but also that the work being carried out will be adversely affected.

With an overload coupling having, in the circumferential direction, equally long coupling projections and coupling recesses, or shorter coupling recesses, on the mutually facing sides of the coupling disks, see for example FIGS. 6 to 8 in DE 197 45 245 A1, there is a danger that after a disengagement resulting from an overload, as a consequence of the inertia of the parts the arresting moment is initially relatively strong and then strongly reduced in an undesired manner. With the configuration according to FIG. 7 of that document, although the coupling projections bounding the coupling recesses have inclined flanks, whereby the rotational engagement in the case of slippage occurs in a less percussive manner and thus softer, there exists however in this configuration the danger that the coupling elements, preferably formed by means of balls, upon slippage of the overload coupling, spring over the respective following coupling recess and reach the then following coupling projection, whereby the transmitted torque is relatively slight.

It is thus further the object of the invention to reduce the negative influence of inertia on the functioning of the overload coupling.

With a treatment instrument according to claim 15 the coupling projections are shorter in the circumferential direction than the coupling recesses. By these means, in functional operation, the coupling elements have more time to again enter into the associated coupling recesses and upon bearing on the then respectively following coupling projection to maintain the torque transmission. Thereby, upon slippage, there is effected a satisfactory torque transmission at the desired level of the torque.

This advantageous function can, by means of further developments of the invention, be stabilised and attained also for greater ranges of speed of rotation. The further developments also contribute to ensuring a slippage of the overload coupling even with slight variation of the torque. By these means there are avoided in particular suddenly increasing torque values and thus the loading on the tool is reduced. Suddenly changing torque values are in particular disadvantageous with such tools as are sensitive and tend to break, as is the case with tools for the preparation of a root canal of a tooth.

There is thus effected, in functional operation, a softer slippage of the overload coupling, with reduced torque fall-off, by means of which the above-described loading peaks are avoided or at least reduced. With the configuration in accordance with the invention it is equally advantageous whether the rearward or the forward coupling part manifests the characterising features of the invention.

Features disclosed herein contribute the attainment of the object of the invention and lead to simple, economically manufacturable and simply and rapidly installable or disinstallable configurations, whereby a good functioning is ensured and small manufacturing costs are attained.

BRIEF DESCRIPTION OF THE DRAWINGS

Below, the invention and further advantages which can be achieved thereby will be described in more detail with reference to advantageous configurations of an exemplary embodiment. There is shown.

DETAILED DESCRIPTION OF THE PRESENTLY PREFERRED EMBODIMENTS

Figure 1:
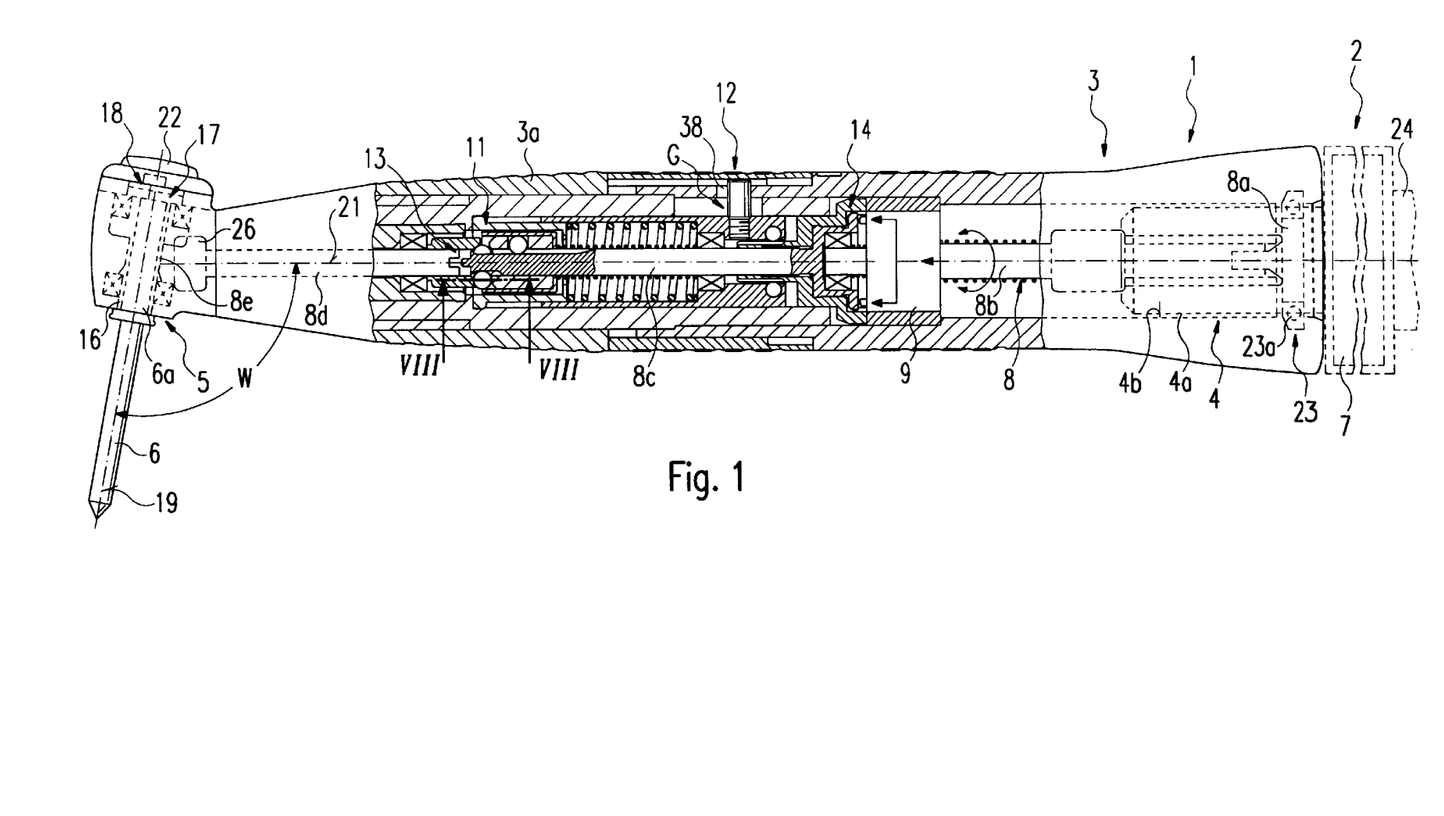
FIG. 1 a treatment instrument in accordance with the invention, in axial section.

The main parts of the treatment instrument, designated generally as 1, are a connecting part 2 forming the rearward end of the treatment instrument, the handpiece 3 which is releasably connected with the connecting part 2 by means of a quick-fastening coupling 4 in the form of a plug-in coupling and, in the coupled-together condition, extends forwardly from the connecting part 2 in a rod-like manner in the form of a grip sleeve 3a, a tool holder 5, arranged at the forward end of the handpiece 3, for a treatment or working tool 6, in particular a root canal tool, a preferably electric drive motor 7 in the connecting part 2, a drive shaft train designated overall as 8, which extends longitudinally through the handpiece 3 forming the grip sleeve, and which is of a plurality of drive shaft sections 8a, 8b, 8c, 8d, 8e which in each case are connected or connectable with one another by means of a coupling, a step-down transmission 9 associated with the drive shaft chain 8 in the region of the connecting part 2 or of the handpiece 3, an overload coupling 11 associated with the drive shaft chain 8 in the region of the connecting part 2 or of the handpiece 3, which restricts the torque transmission to a particular torque value, a first setting device 12 with which this torque value can be changed and thus with which the overload coupling 11 is settable, and a direct coupling 13, arranged in the region of the overload coupling 11, which by means of a second setting device 14 can be selectively engaged or disengaged. The handpiece 3 extends preferably in a straight manner. It may, however, also extend in an angled manner, as is per se known.

The tool holder 5 has, in the case of the present exemplary embodiment, a receiving sleeve 16, forming the forwardmost drive shaft section 8e, into which the tool 6 can be inserted with its tool shaft 6a and releasably connected with receiving sleeve 16 by means of a rotary coupling 17 and an axially effective retaining coupling 18. The middle axis 19 of the receiving sleeve 16, and also of the tool 6, is directed transversely to the longitudinal middle axis 21 of the handpiece 3 or the treatment instrument 1, whereby between these middle axes 19, 21 at the side of the tool 6 an obtuse angle W of about 90° to about 100° or an angle W of about 90° or about 100° is included.

For releasing the retaining coupling 18, an actuating member 22 is arranged on the side of the handpiece end, here thickened in the manner of a head, away from the tool 6, which actuating member is here preferably mounted to be coaxially displaceable and with a movement of the coupling element caused by finger pressure displaces the retaining coupling 18 into its decoupling disposition releasing the tool shaft 6a. The rotary coupling 17 and the retaining coupling 18 are per se known couplings so that a detailed description is not necessary.

The quick-fastening coupling 4 is preferably formed by means of a plug-in coupling which releasably latches in the plugged-together disposition. Preferably, this plug-in coupling is so formed that in the plugged-together disposition the drive part 2 and the handpiece 3 are mounted to be freely rotatable relative to one another around the longitudinal middle axis 21. By these means the manipulability of the handpiece 3 is substantially improved, because the connecting part 2 does not need to take part in rotating movements of the handpiece 3 during the treatment. The so-formed turn/plug-in coupling has a hollow cylindrical coupling pin 4a on the one coupling part and a coupling recess 4b which receives this with slight play for movement. With the present configuration, the coupling pin 4a extends forwardly from the connecting part 2 and the coupling recess 4b is arranged in the rear end region of the handpiece 3. For latching in the coupling disposition there serves a latching device 23, which can be overcome, having a latching element 23a which is arranged in a recess in the outer surface of the plug-in pin 4a or in the inner surface of the plug-in recess 4b and by means of a spring so engages into a latching recess arranged in each case oppositely in the other part that the latching device 23 can be overcome and released by an axial pulling force which can readily manually be applied.

The connecting part 2 is connected by means of a schematically illustrated flexible supply hose 24 with a non-illustrated control apparatus, as is usual for a dental treatment station. There extends through the supply line 24 a current supply line for the drive motor 7 and possibly media lines having lines for air, water and/or spray, which pass through the quick-fastening coupling 4, in a manner known per se, so that they are functional and sealed in any rotational position, and extend up to the forward end region of the handpiece 3, where they open out and are directed towards the treatment site. For reasons of simplification, these lines are not illustrated.

The first drive shaft section 8a extends from the drive motor 7 up to the region of the quick-fastening coupling 4 where it is connected with the second drive shaft section 8b by means of plug-in coupling elements engaging into one another in a form-fitting manner, which upon plugging together of the quick-fastening coupling 4 are simultaneously and self-actingly coupled. The second drive shaft section 8b extends forwardly up to the step-down transmission 9, which is connected with the third drive shaft section 8c by means of an axial slide coupling 25. This shaft section extends up to the overload coupling 11 which is located in the middle region of the handpiece 3. From the overload coupling 11 there extends the fourth drive shaft section 8d which is coupled with the receiving sleeve 16, forming the fifth drive shaft section 8a, by means of a toothed gear transmission or a bevelled gear transmission 26, by means of which the rotary drive of the receiving sleeve is ensured. It is also possible to provide such a transmission that the rotary movement of the drive shaft section 8d is converted to an axial movement of the receiving sleeve 16, whereby an axial stroke drive is provided for the tool 6. It is further also possible to so form the transmission 26 that it drives the receiving sleeve and thus also the tool 6 in the manner of an axial stroke movement and rotary movement.

The drive shaft sections 8a to 8e are each mounted rototably by means of suitable bearings, preferably conventional roller or ball bearings.

Figure 2:
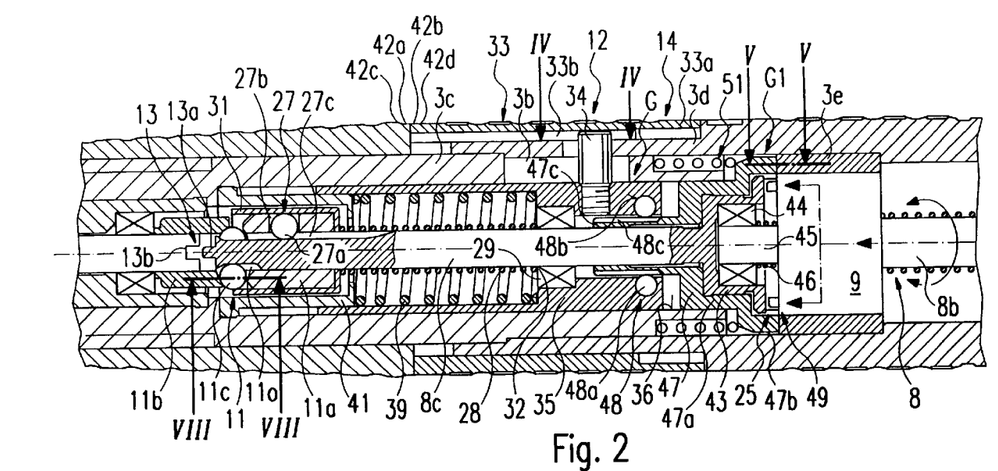
FIG. 2 an axial detail of the treatment instrument, in section and in an illustration to an enlarged scale, in a first functional disposition.

The overload coupling 11 is formed by means of two coupling sleeves or disks 11a, 11b, of which the rearmost coupling disk 11a has at its forward side, and the forwardmost coupling disk 11b has at its rearward side, in each case at least one coupling element, whereby the coupling elements engage into one another in a form-fitting manner and are so formed with oblique or rounded flanks that when a certain torque is exceeded they yield axially relatively so that the overload coupling is overcome and thus a larger torque is no longer transmitted. With the present exemplary embodiment, one of the two coupling disks, here the rearward coupling disk 11a, is mounted axial displaceably on the drive shaft section 8c, connected fixed for rotation by means of rotary connection 27 with the drive shaft section 8c and biased by means of a pressure spring 28 in the direction towards the forward coupling disk 11b. The pressure spring 28 is arranged behind the coupling disk 11a on the drive shaft section 8c, whereby its rearward end is axially supported at a rotary bearing 29 of the drive shaft section 8c. With the present exemplary embodiment, the rotary connection 27 has a connection element 27a, preferably formed by means of a ball, which sits in a radial hole 27b in the coupling disk 11a and engages in a form-fitting manner in a longitudinal groove 27c in the drive shaft section 8c. The connection element 27a is prevented from radially drifting out of the hole 27b by means of a pot-like sleeve 31, the circumferential wall of which radially covers over the hole 27b.

Figure 8:
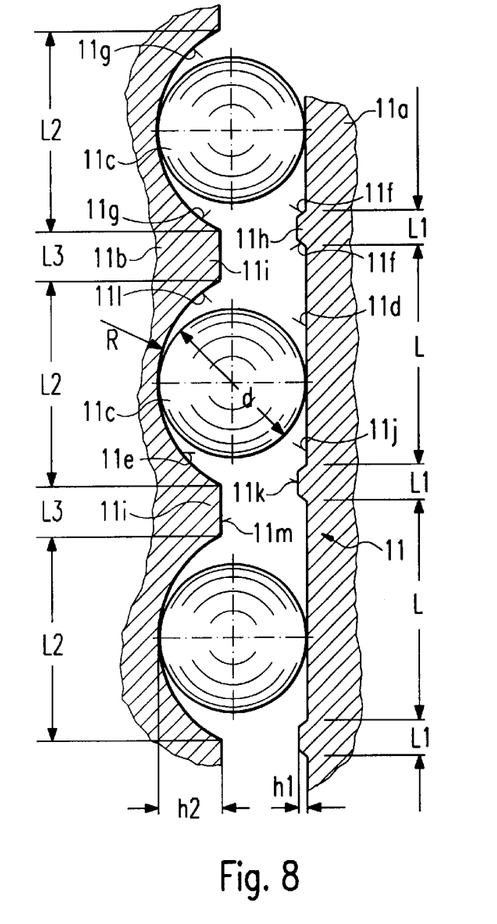
FIG. 8 the partial section VIII—VIII of FIG. 2.

With the present exemplary embodiment the overload coupling 11 has a plurality of coupling elements 11c, for example three, in particular formed by balls, arranged evenly distributed on the circumference, which elements in each case sit in a first coupling recess 11d in the coupling disk 11a and in a second coupling recess 11e in the second coupling disk 11b. FIG. 8 shows the section VIII—VIII in a developed view. The coupling recesses 11d, 11e are bounded in the circumferential direction by the flanks 11f, 11g of first and second coupling projections 11h, 11i on the first and second coupling disks 11a, 11b. With the present exemplary embodiment the coupling recesses 11d of the first coupling disk 11a are formed by means of radial grooves, angular, for example trapezoidal in cross-section, whereby oblique flanks 11f on the coupling projections 11h are provided. The plane base surfaces of the coupling recesses 11f are designated by 11j and the preferably plane top surfaces of the coupling projections 11h are designated by 11k. The base and top surfaces of the coupling disk 11b are designated by 11l, 11m.

It has proved to be advantageous to dimension the circumferentially directed length of the coupling recesses 11d about six times as long as the length L1 of the coupling projections 11h. Thereby, the length L of the coupling recesses 11d may be about double the diameter d of the coupling elements 11c. The depth of the coupling recesses 11d, or the height h1 of the coupling projections of the one coupling disk 11a, here the axially moveable coupling disk 11a, is smaller than the height h2 of the other coupling disk 11d. Moreover, it is advantageous to provide the coupling recesses 11e of the other coupling disk 11b, here the axially non-moveable coupling disk, with a rounded cross-sectional shape, in particular a cross-sectional shape in the form of a section of a circle.

With the present exemplary embodiment, in which the diameter of the coupling elements 11c is about 1.5 mm, the height h of the coupling projections 11h is in each case about 0.1 mm, the length L of the coupling recesses 11d running in the circumferential direction is about 2.5 mm and the length L1 of the coupling projections 11h is about 0.5 mm. On the other or forward coupling disk 11b, having the preferably rounded coupling recesses 11e, the radius R of the rounded coupling recesses 11e is in each case about 1.5 mm, whereby a height h2 of about 0.6 mm is provided for the associated coupling projections 11i. Thereby, further, there is provided a length L3 of the associated coupling projections 11i which is greater than length L1 of the coupling projections 11h of the other coupling disk 11a whereby the length L2 of the coupling recesses 11e of the preferably axially non-displaceable coupling disk 11b is smaller than the length L of the one coupling disk 11a.

By means of this configuration it is provided that when the overload coupling 11 is overcome or slips, the coupling elements 11c in each case again dip into the coupling recess 11d lying next thereto in circumferential direction, and thereby a largely uniform maximum torque value is transmitted upon slippage. Thereby, the coupling elements 11c have, after jumping over the next coupling projections 11h, more time to stabilise in the following coupling recesses 11d. The oblique or preferably rounded flanks 11g and higher coupling projections 11i on the other coupling disk 11b are intended to synchronise the coupling elements 11c and upon arrival at the next coupling projections 11i have a damping effect on the force development. The rolling friction thereby possible provides, even with unfavourable lubrication conditions, uniform catching moments. Also, the influence of the speed of rotation on the torque can be kept within tolerable limits. This means that the configuration in accordance with the invention is suitable also for higher ranges of speeds of rotation.

With the present exemplary embodiment, the rearward coupling disk 11a has the coupling recesses 11d having the greater length L. On the other hand, the coupling projections 11e of the axially non-moveable coupling disk 11b are rounded. By these means the advantage is attained that the axially moveable coupling disk 11a carries out axial movements of only slight length upon slippage of the overload coupling 11.

Figure 9:
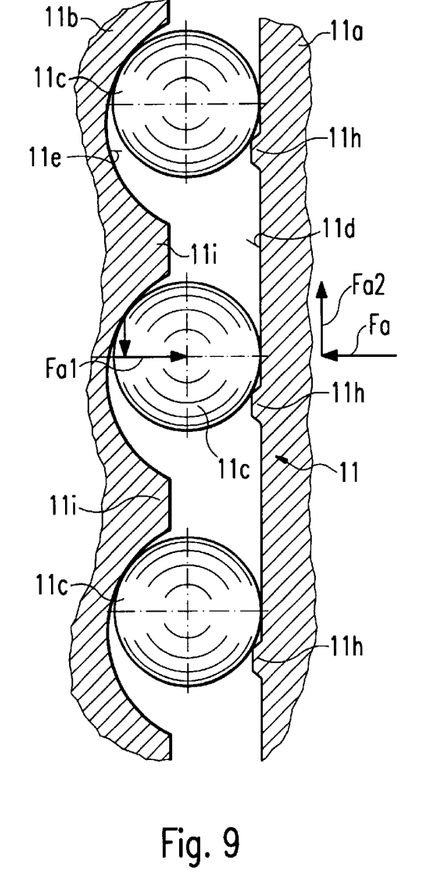
FIG. 9 the partial section VIII—VIII of FIG. 2 in a different functional disposition.
Figure 10:
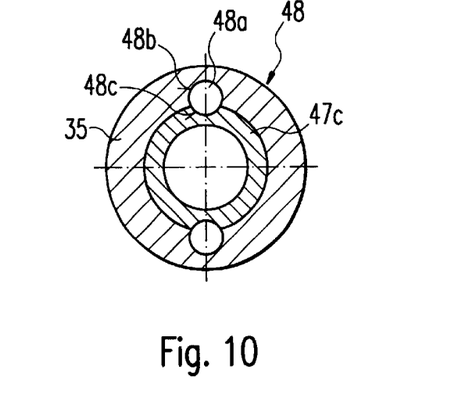
FIG. 10 the partial section X—X of FIG. 3.

Within the scope of the invention the above-described features may be arranged with regard to the axially moveable and axially non-moveable coupling disk but, however, may be arranged vice versa. The coupling elements 11c are preferably of a material of low relative density, in particular ceramics material, whereby good running and emergency running properties, and low mass, are attained. FIG. 8 shows the parts of the overload coupling 11 in a neutral position, in which no resistance is effective on the tool 6. When, in functional operation, a resistance is effective on the tool 6, the coupling parts 11a, 11b take up the position illustrated in FIG. 9, in the case of clockwise running, in which the coupling projections 11h bear on the coupling elements 11c and these bear on the coupling projections 11i. As soon as the resistance, and thus the torque transmitted between the coupling disks 11a, 11b, exceeds a particular value the coupling projections 11h are displaced on and over the coupling elements 11c, whereby the coupling disk 11a is initially moved axially backwards and then again move forwards, so that the coupling projections 11h again dip between the coupling elements 11c or the latter dip into the coupling recesses 11d and thus in each case reach the fore of the next coupling resistance in the circumferential direction. Before, however, the torque reaches the predetermined value, the coupling elements 11c are moved into the coupling position illustrated in FIG. 9, whereby they roll up on the rounded flanks 11g and remain in a position in which the flanks 11g apply against the coupling elements 11c a resistance force component Fa1, which is increased by the axial biasing force Fa, and increases the torque Fa2 effectively transmissible between the coupling elements 11c and the coupling projections 11h, 11i in the circumferential direction. Thereby it is ensured that the coupling elements 11c do not roll over the coupling projections 11i, but that the coupling projections 11h roll over the coupling elements 11c. The coupling projections 11i with their rounded flanks 11g, or the associated coupling recesses 11e, thus form holding elements for the coupling elements 11c so that the latter, upon slippage of the overload coupling 11, remain in the coupling recesses 11e.

The coupling elements 11c can additionally engage into longitudinally grooves 11o in the drive shaft section 8, by means of which the rotary connection is stabilised or ensured.

Figures 3, 6:
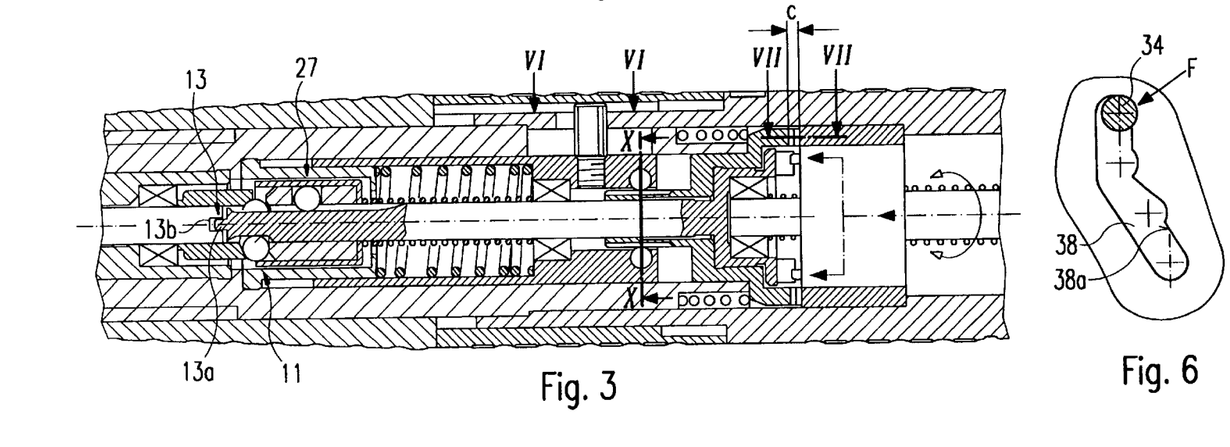
FIG. 3 the section according to FIG. 2 in a different functional disposition.
FIG. 6 the partial section VI—VI of FIG. 3.

The direct coupling 13 has a projecting transverse web 13a on the one coupling part formed by means of the drive shaft section 8c and has a transverse groove 13b on the other coupling part formed by means of the coupling shaft section 11d. The transverse web 13a can be inserted into the transverse groove 13b for the purpose of engaging the direct coupling 13. This is effected by means of an axial displacement of the preferably rearward drive shaft section 8c, which is possible by means of the slide coupling 25 and will be described further below.

With the first setting device 12, the compression tension with which the coupling disks 11a, 11b are biased against one another, or their elastic yieldability, can be altered and consequently so set that the overload coupling 11 opens, in this case slips, at different torque values. With the present configuration, the biasing of the spring 28 is altered, or reduced or increased, with the setting device 12. This is effected in that the counter-bearing 32 of the spring 28 is axially displaceable and fixable in the respective displaced position. For this purpose there serves a manually externally actuable setting member 33 which radially inwardly penetrates the handpiece 3 or grip sleeve 3a with a connection member 34 and is connected with a slider 35 arranged in the handpiece 3 which slider upon its axial displacement forwardly with the setting member 33 likewise displaces the counter-bearing 32 forwardly and thereby increases the biasing of the spring 28. Upon a displacement of the setting member 33 in the opposite direction, the counter-bearing 32 mounted axially displaceably in the handpiece 2 automatically follows the slider 35 rearwardly under the spring tension, whereby the biasing of the spring 28 is reduced. The displacement or alteration of the torque value can be effected steplessly or in steps. For fixing in the respective adjusted position of the slide guide present, there may be provided for example a clamping or fixing element. With the present configuration, the setting member 33 is a rotary ring 33a or a rotary sleeve surrounding the grip sleeve 3a. The connection member 34 is formed by means of a radially arranged switching pin which is screwed into the slider 35 with its inward end. The rotary connection between the setting member 33 and the connection member 34 can be formed by means of a longitudinal groove 33b at the inner side of the setting member 33 into which the connection member 34 engages.

The slider 35 is mounted axially displaceably and non-rotatably, with a slight play for movement, in a longitudinal bore 36 in the grip sleeve 3a. For this purpose the connection member 34 can engage with play for movement into a longitudinal groove 3b in the inner wall of the grip sleeve 3a or of an inner sleeve 3b sitting therein. The hollow cylindrically formed setting member 33 of the rotary ring 33a is, with its inner circumference, rotatably mounted on a tapered cylindrical bearing section 3d of the grip sleeve 3a. A transmission G is provided which converts the rotary movement of the rotary ring 33a into an axial movement of the slider 35 which transmission is formed by means of setting groove 38 (FIG. 4), developing in the circumferential direction obliquely or in a curve shape, in this bearing section 3d. The connection member 34, for example formed by means of a pin or a screw, engages into a longitudinal groove 36 at the inner side of the rotary ring 33a The slider 35 and rotary bearing 29 form a movement unit, whereby the outer ring of the rotary bearing 29 is displaceably mounted, with slight play for movement, in the drive shaft section 8c and can bear against a rearward shoulder should surface in the slider 35. The spring 28 bears rearwardly on the slider 35 indirectly via the rotary bearing 29. Further, there may be provided a spring 39, preferably formed by mean of a compression coil spring, which bears on the forward end of the bore 36 or in the a sleeve 41 emplaced therein, in the grip sleeve 3a or inner sleeve 3c, and biases the slider 35 rearwardly against the guide surface 38a of the setting groove 38. Upon a manual rotation of the rotary ring 33a, the slider 35 or the counter-bearing 32 is axially displaced due to the oblique or curved development of the guide surface 38a which forms a guide for the connection member 34, and thus the biasing of the spring 298 and the torque value are correspondingly changed and set, namely increased or decreased.

Figures 4, 5:
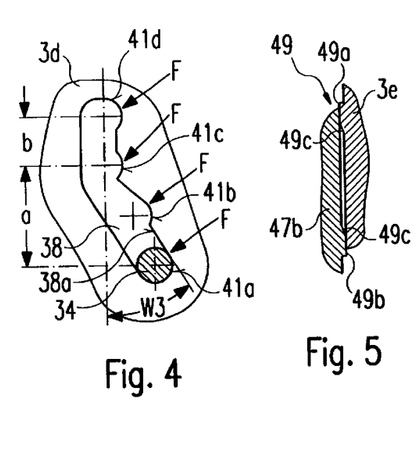
FIG. 4 the partial section IV—IV of FIG. 2.
FIG. 5 the partial section V—V of FIG. 2.
Figure 7:
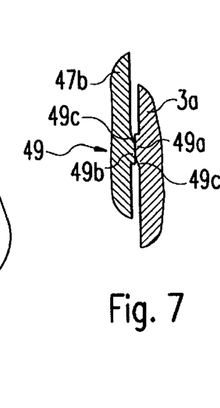
FIG. 7 the partial section VII—VII of FIG. 3.

With a development of the one acute angle W3 of for example 15° to 45° with a guide surface 38a, without self-locking means, containing a transverse plane, and/or if, over the setting path particular setting stages are to be perceptible by means of resistance points, latching recesses 41a, 41b, 41c are arranged in the setting groove 38, into which the pin-like connection member 34 latches under the biasing of the spring 28 and/or 39, whereby the setting is positioned, in manner which can be manually overcome, or whereby the setting steps are manually perceptible. By these means there are formed releasable or surmountable fixing devices F for the setting device 12. FIGS. 4 and 6 show the setting groove 38 in a developed view. The latching recesses 41a, 41b, 41c may also be provided at the left edge of the setting groove 48, if the spring 28 and/o r 39 is effective forwardly.

It is advantageous to associate with the setting member 33 a scaling having a graduation field 42a and complementary scaling or an index 42b on the outer surface of the grip sleeve 3a and on the setting member 33, which allows particular settings of the torque value, on the one hand to be possible and on the other to be readable. With an adjustability of the setting member 33 in the axial direction, the scaling is likewise axially directed. With the rotary ring 33a, the scaling is directed in the circumferential direction.

For the purposes of adaptation to root canal cross-sections of different sizes, there are root canal tools 6 of differing cross-sectional sizes which for better differentiation are designated with a coloured or other marking, for example marking characters, in particular on their preferably uniformly large shafts 6a. It is therefore advantageous and serves for ready handling if there are provided on the setting member 33 or on the grip sleeve 3a one or more coloured or other markings 42c on the setting path, which are so arranged that upon positional alignment with an index 42d, in each case arranged on the other part, a torque value is set which corresponds to the root canal tool 6 of the same colour or of the same marking. By these means there is provided a simplified manner for setting the handpiece 2 to the size or to the kind of at least one root canal tool.

Upon overloading, for example when the tool 6 jams, the overload coupling 11 slips or opens, whereby the transmissible torque is limited and the tool 6 is protected from overloading, in particular from breakage. The marking 42c and the index 42d can be integrated in the scaling 42a, 42b. It is further advantageous to so arrange the at least one marking 42c, 42d that it coincides with an or the associated latch positions 41a, 41b, 41c, whereby the setting is further simplified.

As for the markings 42c, 42d, the latch points 41a, 41b, 41c may be arranged in positions on the adjustment path which correspond to particular torque values, in particular of the associated differing tools 6. Preferably, the markings 42c are associated with the latch points 41a, 41b, 41c.

The first setting device 12 for setting the desired torque value of the overload coupling 11 and the second setting device 14, for engaging or releasing the direct coupling 14, may each be provided with an associated setting member or preferably may be provided with a common setting member 33, as is the case with the present exemplary embodiment. When a setting member which is displaceable in the circumferential direction is present, there is needed a second movement conversion transmission G1, in order to transform the circumferentially directed movement of the setting member 33 into an axial movement of the movable coupling element 13a of the direct coupling 13. With the present exemplary embodiment, the drive shaft section 8c is mounted to be axially movable back and forth by a sufficient amount with its forward direct coupling web 13a, and thereby, by means of the slide coupling 25 is permanently connected for rotation with the drive shaft section 8b or with the drive output part of the step-down transmission 9. The slide coupling 25 may be formed by means of a claw coupling with appropriate length of the inter-engaging claws, for example by means of two mutually opposing pairs of claws.

The drive shaft section 8c has at its rearward end a pot-like bearing part 43 in the rearwardly opened hollow space of which there is arranged a rotary bearing 44, in particular a roller bearing, which sits on a forward bearing pin 45 of the step-down transmission, is axially displaceable thereupon and is biased in an elastically yielding manner in the direction towards the direct coupling recess 13b by means of a compression spring 46 arranged between the bearing pin and the step-down transmission 9.

Further, the drive shaft section 8c is connected to rotate with the slider 35 or the setting member 33 by means of a rotary carrier 47. Thereby, the rotary carrier 47 is longitudinally displaceably connected by means of a slide coupling, designated overall as 48, to the slider 35 and also with the drive shaft section 8c. The rotary carrier 47 has the form of a pot-like body which with its circumferential wall 47a can surround and mount the bearing part 43. Between the free edge 47b of the rotary carrier 47 and a base part 3a mounted to be stationary in the handpiece 3 or in the grip sleeve 3b, for example a base ring surrounding the step-down transmission 9, there is arranged at least one cam transmission 49 for axially displacing the carrier 47, which comes to function when the carrier 47 is rotated beyond the latch point range designated by a. For this purpose, the setting groove 38 has an extension b directed circumferentially. The cam transmission 49 is formed by means of cams 49a, 49b on the base part 3a and on the edge 47b of the rotary carrier 47. Preferably there are provided two cam pairs lying diametrically opposite one another, with cams 49a, 49b. The running surfaces 49c of the cams 49a, 49b are formed to be oblique or rounded. The spacing between the cam transmission 49, which is curved in the circumferential direction, is greater than the spacing a in the circumferential direction between the latch points 41a to 41c. As a consequence, the direct coupling 13 remains disengaged when the setting member 33 is moved, for setting selected torque values, in the range a of these latch points. When, in contrast, the setting member 33 is moved or rotated beyond this range a, here beyond the third latch point 41c, the cams 49a, 49b meet one another, whereby the rotary carrier 47 is displaced forwardly against the force of spring 51, by an amount c corresponding to the entry depth of the direct coupling element 13a; see the different positions between FIGS. 2 and 3. When, thereby, the direct coupling web 13a, due to a different positioning with reference to the direct coupling recess 13b, cannot latch therein, only the carrier 47 is displaced forwardly whereby the drive shaft section 8c, under the axial biasing of the compression spring 46, self-actingly latches into the direct coupling recess 13b when it is in coincidence with its position. In this functional disposition, the overload coupling 11 is switched off or bypassed by means of the direct coupling 13, whereby the drive shaft section 8d or the tool 6 can be driven with the maximum available torque. In order to stabilise this disposition of the setting device 14, it is advantageous to provide in the end region of the extension b of the setting groove 38 a further latch recess 41d for the connecting member 34.

The slide coupling 48 effective between the rotary carrier 47 and the drive shaft section 8c is formed by means of one or more coupling elements 48a, in particular balls, arranged distributed on the circumference, which elements each sit rotatably in a recess 48b in the inner surface of the slider 45 and engage into a longitudinal groove 48c in a bushing 47c of the carrier 47 which projects into the slider 35.

For switching off or disengaging the direct coupling 13, the setting member 33 is turned back to the desired position of the range a, here the latch points 41a to 41c whereby the rotary carrier 47 is pushed back rearwardly into its initial position in accordance with FIG. 5 by means of the compression spring 51, which is arranged in a ring groove of the inner sleeve 3c and is effective between the latter and the rotary carrier 47. Thereby, the drive shaft section 8c is at the same time displaced axially into its decoupling position, whereby the rotary carrier 47 of the pot-like bearing part 43 and thus the drive shaft section 8c is carried along with this axial movement. Due to the spacing between the cam drive 49, appropriately greatly dimensioned in the circumferential direction, in the movement range a, between the latch points 41a to 41c, the direct coupling 13 remains in its decoupled disposition.

The overload coupling 11 and the direct coupling 13 may be equipped for only one direction of rotation, for example clockwise, of the tool 6, or may be equipped for both directions of rotation. In the first case it is sufficient when only the flanks 11f, 11g, facing in the direction of rotation, of the coupling projections 11h, 11i or coupling recesses 11d, 11e are formed as described above. In the second case the flanks 11f, 11g, facing in the other direction of rotation, are likewise formed in accordance with the invention, preferably in a mirror-image manner.

With all above-described exemplary embodiments it is possible to provide, instead of a mechanical torque limitation, an electrical torque limitation, which for example so controls the drive motor 7 in terms of the current strength that a particular maximum torque is not exceeded. Furthermore, there may be provided a electrical setting device for varying the torque value. Thereby, the setting range a can be omitted. For this purpose there may be provided for example on the circumference of the connecting part 2 or on a foot switch, an adjustable setting member at which the variable torque is manually settable.

An electrical control device for limiting the transmissible torque value or also for the setting of this value, can with all above-described embodiments for example be integrated into the non-illustrated control apparatus.

What is claimed is:

1. Handpiece for medical purposes, comprising
   a tool holder disposed in a forward end region of the handpiece,
   a retaining coupling for releasably fixing a tool in the tool holder,
   a drive connection for a rotary and/or stroke drive of the tool holder, extending longitudinally through the handpiece, and
   an arrangement for limiting the maximum torque value that can be transmitted to the tool holder to a lesser torque value,
   wherein that the arrangement can be selectively deactivated and again activated, by means of a setting device, and
   wherein the arrangement comprises an overhead coupling disposed in the drive connection, which limits the transmissible torque to the lesser torque value.

2. Handpiece according to claim 1, wherein the overload coupling is disposed between two drive shaft sections and a direct coupling connects the drive shaft sections to each other.

3. Handpiece according to claim 2, wherein the direct coupling bypasses the overload coupling.

4. Handpiece according to claim 2, wherein the direct coupling is disposed coaxially with the overload coupling.

5. Handpiece according to claim 2, wherein the direct coupling comprises a direct coupling recess, which is non-round in cross-section, and a coupling projection, which is non-round in cross-section and which can be introduced into the coupling recess, at facing ends of the drive shaft sections.

6. Handpiece according to claim 5, wherein the coupling projection comprises a transverse coupling web and the coupling recess comprises a transverse coupling groove.

7. Handpiece according to claim 5, wherein one said drive shaft section is a rearward drive shaft section and is axially moveable by means of the setting device.

8. Handpiece according to claim 7, wherein the rearward drive shaft section is biased into a coupling position by the force of a spring.

9. Handpiece according to claim 2, wherein the maximum torque value of the overload coupling can be selectively decreased or increased by means of a setting device, and there is provided a common setting member for engaging and disengaging the direct coupling and for setting the maximum torque value of the overload coupling.

10. Handpiece according to claim 9, wherein the setting member is disposed externally manually accessibly on the handpiece.

11. Handpiece according to claim 10, wherein the setting member is moveable in a circumferential direction of the handpiece and the handpiece further comprises, disposed between the setting member and the direct coupling a movement conversion transmission which transforms circumferentially directed movement of the setting member into an axially directed movement of the moveable coupling element of the direct coupling.

12. Handpiece according to claim 11, wherein the setting member is formed by a rotary ring.

13. Handpiece according to claim 2, wherein the setting member has a first setting range (a) for setting the maximum torque value of the overload coupling and a second setting range (b), adjoining the first setting range (a), for engaging the direct coupling.

14. Handpiece according to claim 13, wherein the second setting range (b) adjoins the first setting range (a) at the position of the maximum torque value.

15. Handpiece according to claim 2, wherein the setting device is positioned in a manner which can be manually overcome, for setting the maximum torque value and/or setting the direct coupling in the engaged position and the disengaged position of the direct coupling and/or in the setting positions of the overload coupling.

16. Handpiece according to claim 1, comprising a medical or dental treatment instrument.

17. Handpiece for medical purposes, comprising
   a tool holder disposed in a forward end region of the handpiece,
   a retaining coupling for releasably fixing a tool in the tool holder,
   a drive connection, for a rotary and/or stroke drive of the tool holder, extending longitudinally through the handpiece,
   an overload coupling, disposed in the drive connection, which limits the transmissible torque to a maximum torque value, the overload coupling having two coupling disks disposed coaxially to one another, which at their facing sides have coupling recesses having flanks and coupling projections having a height distributed in a circumferential direction, at least one coupling disk being mounted axially displaceably and elastically biased against the other coupling disk and, a coupling roller element disposed in each case in two axially oppositely lying coupling recesses, wherein the coupling projections of at least one coupling disk are shorter than the coupling recesses in the circumferential direction.

18. Handpiece according to claim 14, wherein the coupling recesses of the other coupling disk form retaining elements for the coupling roller elements.

19. Handpiece according to claim 17, wherein the height of the coupling projections of the other coupling disk is greater than the height of the coupling projections of the one coupling disk.

20. Handpiece according to any of claim 17, wherein at least the flanks facing in the direction of rotation, or both flanks of the coupling recesses of the other coupling disk are concavely rounded.

21. Handpiece according to claim 20, wherein the flank roundings have a radius that is greater than a radius of the coupling roller elements.

22. Handpiece according to claim 17, wherein a rearward coupling disk is axially displaceably mounted and is elastically biased against a forward coupling disk.

23. Handpiece according to claim 21, wherein the radius of the flank rounding is 1.5 times the radius of the coupling roller elements.

24. Handpiece of claim 17 comprising a medical or dental treatment instrument.

25. Handpiece of claim 24, wherein the instrument is a dental treatment instrument for removing material of a tooth root canal.

* * * * *